US008064678B2

(12) United States Patent
    Gregson

(10) Patent No.: US 8,064,678 B2
(45) Date of Patent: Nov. 22, 2011

(54) AUTOMATED DETECTION OF CELL COLONIES AND COVERSLIP DETECTION USING HOUGH TRANSFORMS

(75) Inventor: Mark Gregson, Tyne and Wear (GB)

(73) Assignee: Genetix Corporation, San Jose, CA (US)

( * ) Notice: Subject to any disclaimer, the term of this patent is extended or adjusted under 35 U.S.C. 154(b) by 637 days.

(21) Appl. No.: 12/253,163

(22) Filed: Oct. 16, 2008

(65) Prior Publication Data
    US 2009/0129660 A1    May 21, 2009

Related U.S. Application Data

(60) Provisional application No. 60/981,694, filed on Oct. 22, 2007, provisional application No. 60/981,712, filed on Oct. 22, 2007.

(51) Int. Cl.
    *G06K 9/00*    (2006.01)
(52) U.S. Cl. ........................................................ 382/133

(58) Field of Classification Search ........................ None
    See application file for complete search history.

(56) References Cited

U.S. PATENT DOCUMENTS

| | | | | |
|---|---|---|---|---|
| 7,738,730 | B2* | 6/2010 | Hawley | 382/281 |
| 2003/0179916 | A1* | 9/2003 | Magnuson et al. | 382/128 |
| 2010/0074507 | A1* | 3/2010 | Klottrup et al. | 382/133 |
| 2010/0165326 | A1* | 7/2010 | Tomisek et al. | 356/51 |
| 2011/0124037 | A1* | 5/2011 | Backhaus et al. | 435/30 |

* cited by examiner

*Primary Examiner* — Jermele M Hollington
(74) *Attorney, Agent, or Firm* — Kikpatrick Townsend & Stockton LLP

(57) ABSTRACT

The present invention provides methods and systems for automatic detection of the location of cell colonies on a specimen slide, in particular under the coverslip of a specimen slide. Slide scanning can be performed using an automated microscope with motorized axes. The location of the colonies can be determined by image analysis, which is followed by automatically finding metaphase cells and associating them with each colony. The invention also provides an automated, Hough-transform-based method for identifying the location of the slide coverslip and, if desired, analyzing only the image area contained within the coverslip.

58 Claims, 8 Drawing Sheets

Slide Image

Pre-processed Image

Hough Transform

Coverslip Edges Detected

Coverslip Detection using Circular Hough Transform

Slide Image

Pre-processed Image

Hough Transform

Coverslip Edges Detected

Coverslip detected  Colonies detected

Tiled Image Mosaic

AUTOMATED DETECTION OF CELL COLONIES AND COVERSLIP DETECTION USING HOUGH TRANSFORMS

CROSS-REFERENCES TO RELATED APPLICATIONS

The present application claims benefit of two provisional applications: 60/981,712 (Automated Detection of Cell Colonies) and 60/981,694 (Automated Coverslip Detection by Image Analysis Using Hough Transforms), both filed on Oct. 22, 2007, the entire contents of which are herein incorporated by reference.

BACKGROUND OF THE INVENTION

The present invention relates generally to automated microscopy, and more specifically to improvements in the automatic detection of cell colonies' location on a glass sample slide. Additionally, the glass sample slide may be covered with a coverslip that protects cell colonies from contamination and damage. The coverslip area is that area of a specimen slide where most of focus mapping, image capture and image analysis needs to take place, because cell colonies reside underneath the coverslip. Thus the edges of the coverslip, which denote the area of interest for automated microscopy, need to be reliably detected.

At the present, operators typically scan and analyze the entire slide even though colonies of interest may reside only on several isolated spots within the slide. Operators are required to manually identify colonies (by drawing around them) resulting in slow system throughput. Furthermore, focus mapping can be slow or inaccurate due to sparse cell populations on colony slides.

Some existing methods attempt automated cell analysis of biological specimens by detecting candidate objects. Each slide is first scanned at a low microscope magnification. Candidate objects are identified based on their color, size, and shape; and their location is recorded. The candidate objects are then scanned with higher magnification lens. Thresholding and focusing steps are performed, followed by the morphological processing to identify candidate objects of interest by comparing optical features of the candidate object of interest to a target blob. However, those methods do not use morphological methods that enhance the image of the colonies of interest, neither do they associate the metaphases with the colonies. They also do not disclose a coverslip detection.

Some other existing methods create a composite image from smaller images. Subsequent image analysis is performed only over the areas of interest within the composite image. Those methods also eliminate the edges that were created by the overlaps or similar imperfections between the subimages caused by mechanical alignment errors. Substantially, those methods could be viewed as bandwidth saving methods. They do not disclose background subtraction, morphological methods for colony detection, thresholding, association of metaphases with the colonies, or the coverslip detection.

An accurate identification of the edges of a coverslip on a sample slide continues to be a challenge. Presently, detection methods typically scan and analyze the entire slide, i.e. the areas under and outside of the coverslip, which can be inefficient and time-consuming. Or to reduce scan and analysis time the operators need to accurately place the coverslip in the same position on each slide so that a fixed scan area is applicable to all slides.

Some methods for detecting a microscope slide coverslip are known. For example, these methods can detect the coverslip by locating all four coverslip edges when those edges satisfy a set of predetermined criteria. However, those methods are rule-based and time consuming, and are not applicable to detecting a coverslip of unknown size and location.

Yet some other methods use non-linear Hough transforms to detect some features of the cell or objects within the cell (e.g., detecting nucleus centre, plasma membrane, etc.). Those methods also use an adjustment of the pixel intensity level to improve feature accuracy, presumably on the suspect edges of the objects of interest. However, those methods detect a presence of the objects within the cell, but not their precise outline, nor do they detect the edges of the coverslip.

Some other methods detect objects that are similarly shaped using a pre-existing shape library or they detect a grid-like arranged specimens on a slide using Hough transformation. The centroids of the specimen are detected using 2D peak detection algorithms. Column and row orientations are detected followed by the calculation of the overall grid intersection locations. The method can identify the specimens by finding their expected location in the 2D grid. However, those methods do not detect edges of the object (i.e. coverslip edges), neither do they perform any image enhancements, such as, for example, dark field subtraction.

There is therefore a need for systems and methods that accurately and automatically detect the location of the coverslip on a microscope slide as well as the location of cell colonies of interest underneath the coverslip.

BRIEF SUMMARY OF THE INVENTION

The present invention provides methods and systems for automatic detection of the location of cell colonies on a specimen slide, in particular under the coverslip of a specimen slide. Slide scanning can be performed using an automated microscope with motorized axes. Multiple sub-images of the slide can be acquired with a CCD camera, followed by joining the sub-images into a composite image representing the entire scanned area. A focus map can be determined over potential locations of the cell colonies of interest. The location of the colonies can be determined by image analysis, which is followed by automatically finding metaphase cells and associating them with each colony. The invention also provides an automated, Hough-transform-based method for identifying the location of the slide coverslip and, if desired, for subtracting the coverslip edge and mounting compound image off the digital image of the slide.

In one embodiment, a method for an automatic detection of cell colonies, includes: acquiring digital images of sub-areas of a slide; generating background intensity images; forming background-subtracted sub-area images by subtracting the minimum of a morphologically processed image and the original digital image from the original image; generating shrunk sub-area images by shrinking the background-subtracted sub-area images by a predefined scale factor; stitching the shrunk sub-area images into a composite image representing the entire slide; converting the composite image into a binary edge image by the application of an automatic thresholding technique; passing the binary edge image through a Hough transform to produce a Hough space transformed image; analyzing the Hough space transformed image to identify peaks representing a coverslip edge location; subjecting the Hough space transformed image to an inverse Hough transform to convert the peaks back to the edges of the coverslip in the binary edge image; setting to zero all pixels of the composite image outside of the coverslip area; morphologically processing the composite binary edge image; identifying colonies in the composite binary edge image; eliminating unwanted colonies from the composite binary edge image based on their size or morphology; recording the location, size, or binary image masks of the remaining colonies on the slide; generating a map of automatic focusing values over the remaining colonies on the slide using a high power objective; acquiring a plurality of high power images over the remaining colonies on the slide using a high power objective and the map of automatic focusing values; performing metaphase detection; and assigning each detected metaphase to a colony.

In one aspect, the digital images are acquired by a digital camera with a low power or a high power objective at a fixed calibrated focus.

In another aspect, the morphological processing includes: morphologically closing the sub-area image with a small structuring element; and morphologically opening the resulting image with a large structuring element.

In another aspect, the Hough transform is a linear Hough transform configured for a rectilinear coverslip, where the linear Hough transform is based on polar coordinates of a line. Using this approach, the transformed image is analyzed to identify peaks close to 90° and 180° representing horizontal and vertical lines in the binary edge image, and the transformed image is subjected to an inverse Hough transform to convert the peaks close to 90° and 180° back to horizontal and vertical lines representing the edges of the coverslip in the binary edge image.

In yet another aspect, the Hough transform is configured for a curvilinear coverslip, having a substantially circular shape with a known radius R. For this aspect, the Hough transform is based on a weighted circular Hough transform, where the transformed image is analyzed to find the most probable locations of coverslip centers, and the transformed image is subjected to an inverse circular Hough transform to convert the most probable locations of coverslip centers back to the locations in the binary edge image.

In another embodiment, an apparatus for an automatic detection of cell colonies includes: an optical system having a digital camera for acquiring digital images of the slide, a computing unit for storing and processing the digital images of the slide, the computing unit executing a method so as to cause: images of sub-areas of a slide to be acquired by digital camera with a low power objective at a fixed calibrated focus; background intensity images to be generated; a background-subtracted sub-area images to be formed by subtracting the minimum of a morphologically processed image and the original digital image from the original image; shrunk sub-area images to be generated by shrinking the background-subtracted sub-area images by a predefined scale factor; the shrunk sub-area images to be stitched into a composite image representing the entire slide; the composite image to be converted into a binary edge image by the application of an automatic thresholding technique; the binary edge image to be passed through a Hough transform to produce a Hough space transformed image; the Hough space transformed image to be analyzed to identify peaks, representing coverslip edge location; the Hough space transformed image to be subjected to the inverse Hough transform to convert the peaks back to the edges of the coverslip in the binary edge image; all pixels of the composite image to be set to zero outside of the coverslip area; the composite binary edge image to be morphologically processed; colonies in the composite binary edge image to be identified; unwanted colonies from the composite binary edge image to be eliminated based on their size or morphology; the location, size, or binary image masks of the remaining colonies on the slide to be recorded; a map of automatic focusing values over the remaining colonies on the slide to be generated using a high power objective; a plurality of high power images to be acquired over the remaining colonies on the slide using a high power objective and the map of automatic focusing values; metaphase detection to be performed; and each detected metaphase to be assigned to a colony.

In one aspect, all pixels in the mosaic image outside of the coverslip area are set to zero so that only pixels within the coverslip area are considered for analysis.

In yet another aspect, each detected metaphase is assigned to a colony based on the metaphase proximity to the colony center of gravity, radius, and binary mask.

For a further understanding of the nature and advantages of the invention, reference should be made to the following description taken in conjunction with the accompanying figures. It is to be expressly understood, however, that each of the figures is provided for the purpose of illustration and description only and is not intended as a definition of the limits of the embodiments of the present invention.

DETAILED DESCRIPTION OF THE INVENTION

The embodiments of the present invention can be used to automatically detect the location of cell colonies on a specimen slide, as a precursor to automatically finding metaphase cells and associating them with each colony. The location of the colonies is determined by image analysis. The image can be generated by scanning a slide on an automated microscope with motorized x, y and z axes, capturing images at multiple positions with a CCD camera and stitching these images into a mosaic representing the entire scanned area. The embodiments of the present invention may also use a Hough transform to identify the position of coverslips over the specimen slides, whereby the search for the colonies can be limited to the area under the coverslip.

Figure 1A:
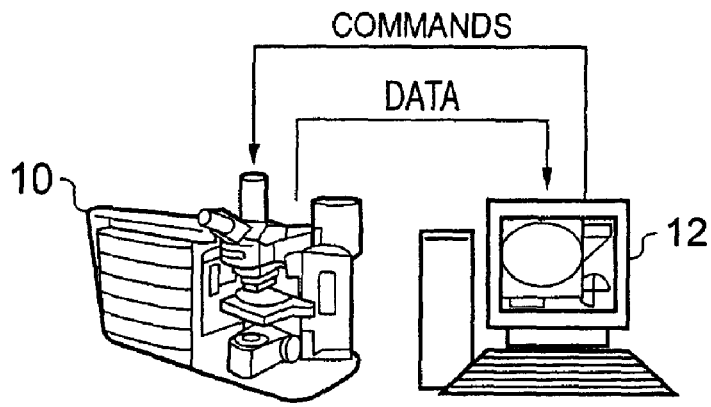
FIG. 1A schematically illustrates a microscope system for capturing images of a sample.

FIG. 1A schematically illustrates a microscope system for capturing images of a sample. The microscope unit 10 captures digital images of a sample under investigation and the digital images are transferred to computer 12 where they are stored. The microscope unit 10 can illuminate the slide with white light for the capturing of bright field digital images, and can also illuminate the slide with a range of specific wavelengths by means of a filter set for the excitation of particular fluorescent emissions.

In some embodiments the slide holding the sample may be loaded manually by a user, but in the illustrated example the microscope unit 10 includes a set of microscope slide racks and an automated slide loader, so that a series of slides may be selected, positioned under the microscope, imaged and returned to the slide racks.

Furthermore, in the illustrated embodiment the computer 12 sends commands to the microscope unit 10 dictating which slides should be imaged, what magnifications they should be imaged at, which light source should be used to illuminate each slide, and so on. Once a series of captured images has been transferred from microscope unit 10 to computer 12, a user operating computer 12 may then examine those images, perform analysis on them, and so on. The example system illustrated is representative of the Ariol® imaging system produced by Applied Imaging corporation Genetix.

Figure 1B:
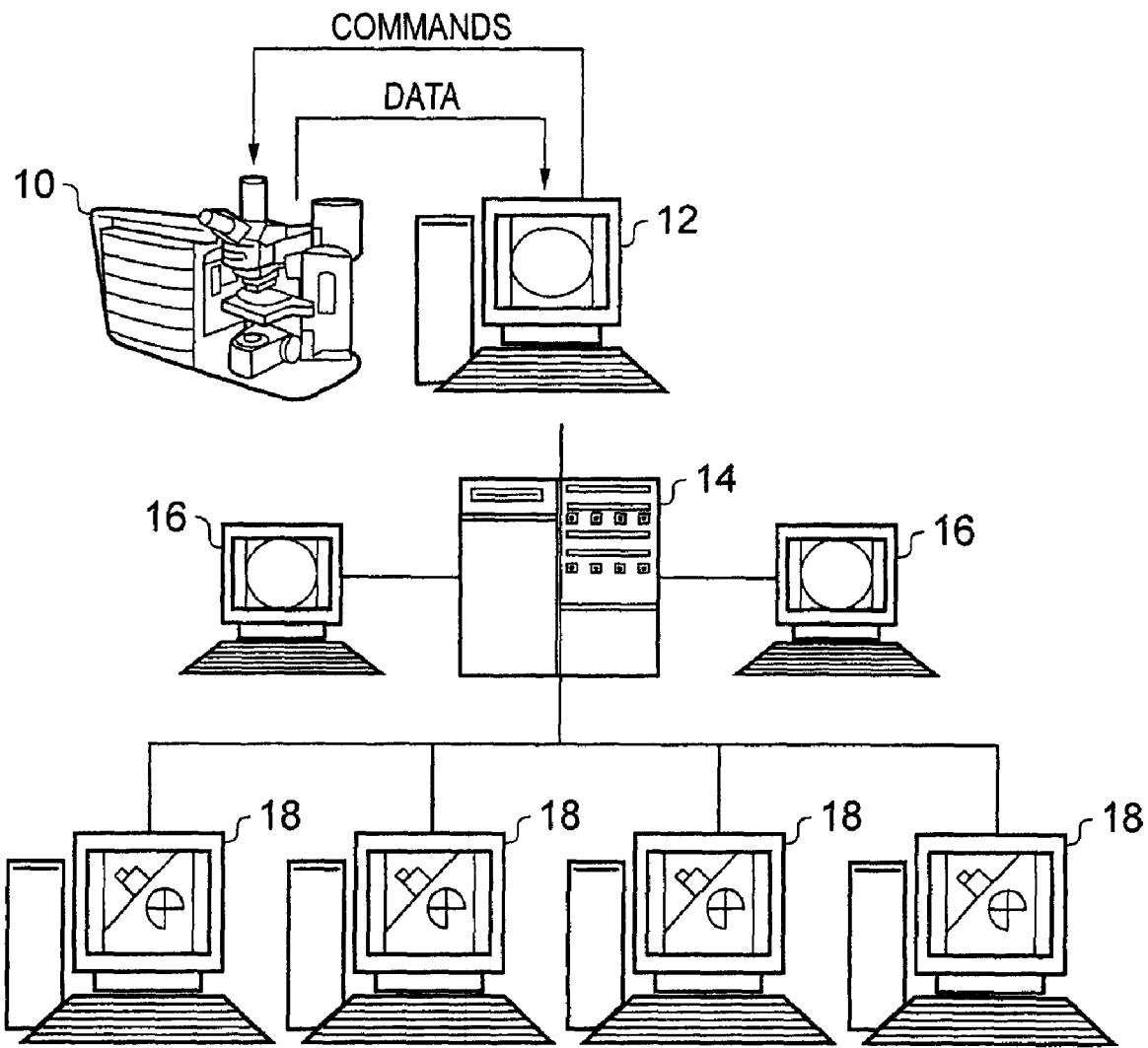
FIG. 1B schematically illustrates the microscope system of FIG. 1A connected to a server and network.

FIG. 1B schematically illustrates the microscope system of FIG. 1A connected to a server 14 and a network. The network consists of both computing devices 16 connected locally to the server 14, and of computing devices 18 located remote from the server 14, for example in a local area network (LAN) or via the internet. In the arrangement illustrated in FIG. 1B the captured images taken by microscope unit 10 are uploaded from computer 12 to the server 14, such that any of the other computing devices 16 or 18 connected to the server 14 may also view those captured images, perform analysis on them etc.

Figure 2:
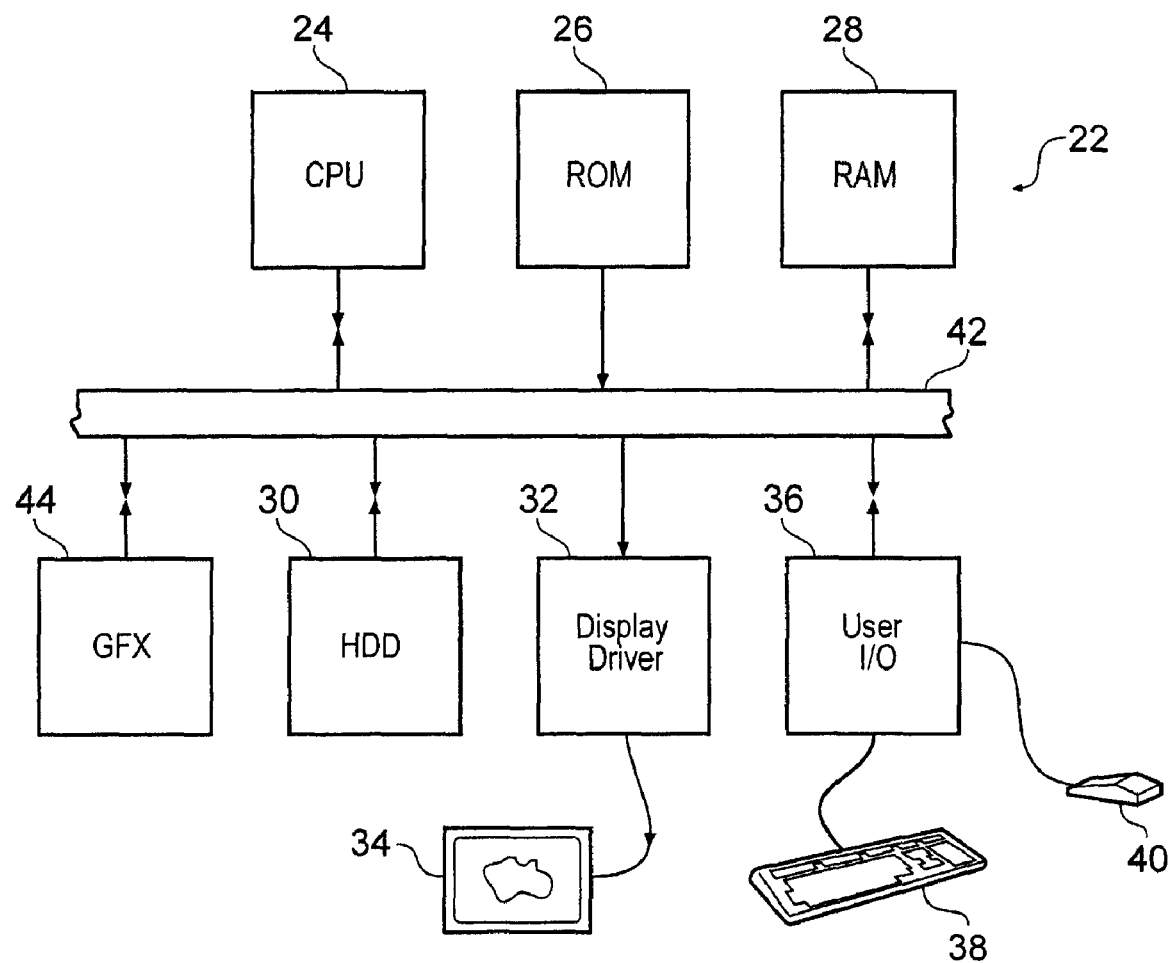
FIG. 2 schematically illustrates a general purpose computer.

FIG. 2 schematically illustrates a general purpose computer system 22 (such as computers 12, 16 or 18 in FIGS. 1A and 1B) configured to process captured images in accordance with an embodiment of the invention. The computer 22 includes a central processing unit (CPU) 24, a read only memory (ROM) 26, a random access memory (RAM) 28, a hard disk drive (HDD) 30, a display driver 32 and display 34, and a user input/output (I/O) circuit 36 with a keyboard 38 and mouse 40. These devices are connected via a common bus 42. The computer 22 also includes a graphics card 44 connected via the common bus 42. The graphics card includes a graphics processing unit (GPU) and random access memory tightly coupled to the GPU (GPU memory) (not shown in FIG. 2).

The CPU 24 may execute program instructions stored in the ROM 26, in the RAM 28 or on the hard disk drive 30 to carry out processing of captured images, for which associated data may be stored within the RAM 28 or the hard disk drive 30. The RAM 28 and hard disk drive 30 are collectively referred to as the system memory. The GPU may also execute program instructions to carry out processing of captured image data passed to it from the CPU.

Figure 3:
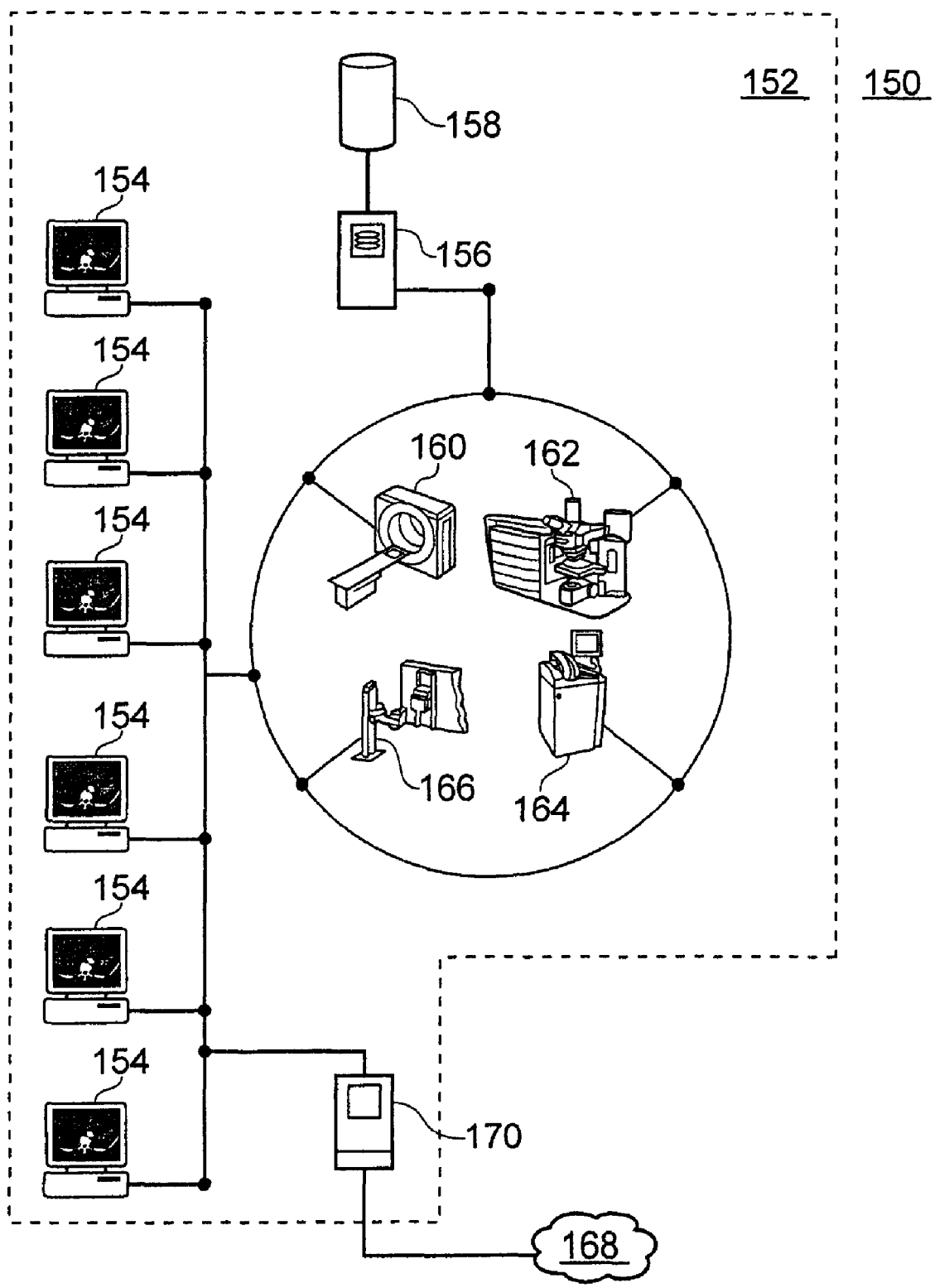
FIG. 3 schematically illustrates medical imaging devices being connected to a hospital computer network.

FIG. 3 shows medical imaging devices and a computer network which can be used in conjunction with embodiments of the invention. The network 150 includes a local area network in a hospital 152. The hospital 152 is equipped with a number of workstations 154 which have access, via a local area network, to a hospital computer server 156 having an associated storage device 158. An archive is stored on the storage device 158 so that data in the archive can be accessed from any of the workstations 154. One or more of the workstations 154 has access to a graphics card and to software for computer implementation of methods of client-side multi-component image composition as described hereinafter. The software may be stored locally at each workstation 154, or may be stored remotely and downloaded over the network 150 to a workstation 154 when needed. Also, a number of medical imaging devices 160, 162, 164, 166 are connected to the hospital computer server 156 and imaging data collected with the devices 160, 162, 164, 166 can be stored directly into the PACS archive on the storage device 156. Of particular interest in the context of the present invention are the captured images from microscope unit 162. The local area network is connected to the internet 168 by a hospital internet server 170, which allows remote access to the PACS archive. This is of use for remote accessing of data and for transferring data between hospitals, for example, if a patient is moved, or to allow external research to be undertaken. One example use would be for a clinician to access and review sample images, such as a pathologist with tissue sample images.

Further details of an exemplary embodiment of the present invention are explained with reference to FIGS. 4-5. One of the problems in detecting colonies and associated metaphases is in deciding which slide area to analyze in detail and which to exclude from the analysis, thus reducing processing time and the possibility of making identification mistakes.

Figure 4:
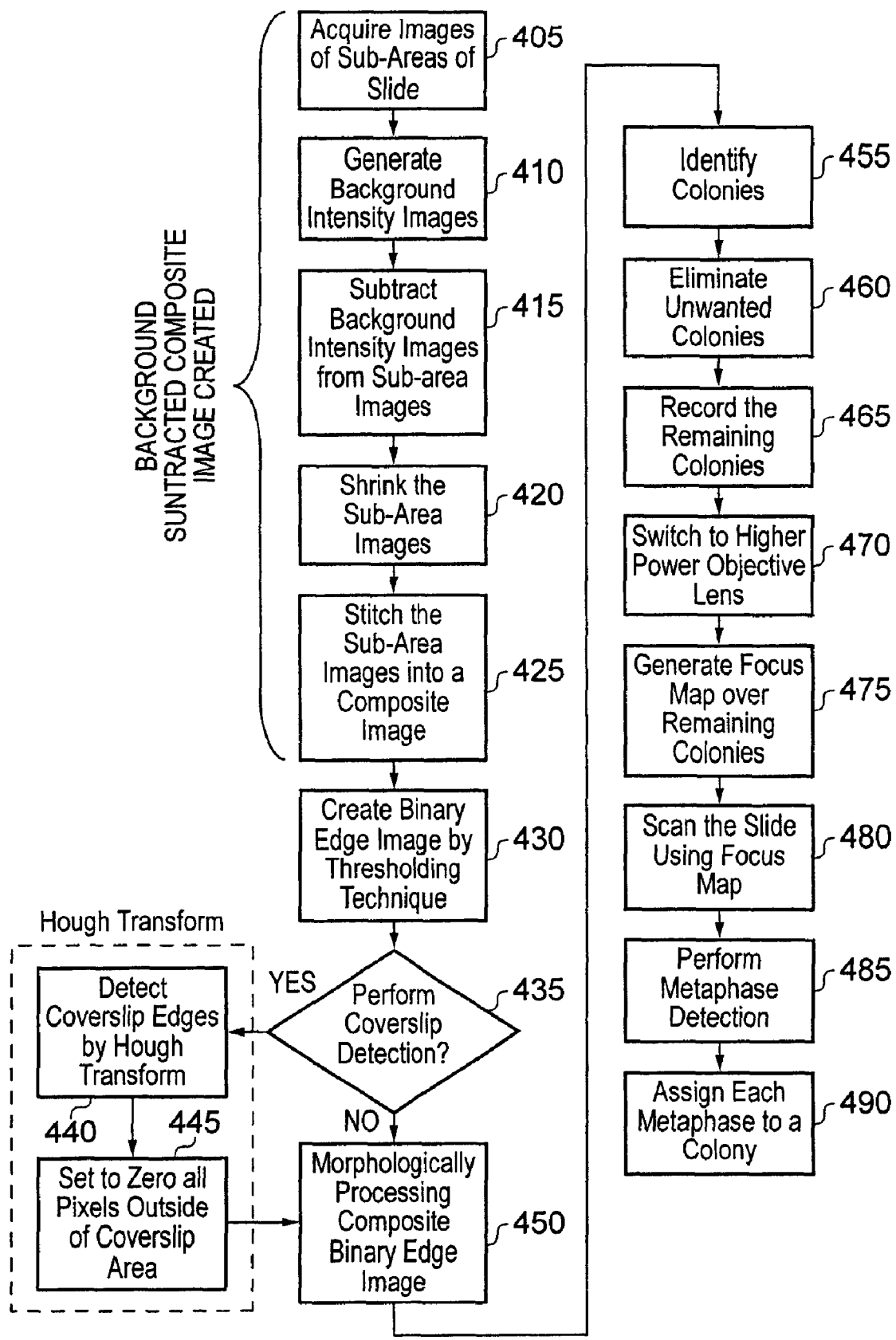
FIG. 4 shows a flowchart of a method for the detection of colonies on a slide.

FIG. 4 shows a flow chart of a method for image acquisition and colony detection according to one embodiment of the present invention. Such a method may be computer-implemented and may be a part of an apparatus as shown and described in FIGS. 1-3 above. The method of the present invention can be implemented as a part of software suite provided by the assignee of the present patent application, for example, the assignee's Cytogenetics software, which is a part of the assignee's CytoVision Systems, within which the invention may be embodied. Such a software suite can also be used as a part of the assignee's Ariol Image Capturing System within which the invention may be embodied. The Ariol Image Capturing System is a high throughput automated image analysis system for the quantification of biomarkers on microscope slides in research, clinical, pharmaceutical, genomic, and proteomic applications. Capable of both brightfield and fluorescent imaging, it rapidly scans and quantifies IHC, FISH, Immunofluorescence, Micrometastasis, Angiogenesis, DNA Ploidy, and Tissue Micro Array slides. Ariol is FDA cleared for in vitro diagnostic use of HER-2/neu, ER, and PR IHC and the detection of micrometastases in bone marrow. In addition to the systems described above, alternative devices that may be used to generate the image of the entire scanned area include, for example, a linescan camera.

At step 405 digital images of a specimen slide are acquired by, for example, a CCD camera. Multiple sub-area of the specimen can be imaged using a low power objective digital camera with a fixed calibrated focus. A linescan camera can be used instead of the CCD camera.

At step 410 The background intensity image can be estimated by morphologically closing the image with a small structuring element to remove noise and then morphologically opening the result with a large structuring element to remove large objects and leave only the background. The operations described here refer to grey value morphology performed over grayscale images. Closing is the process of image dilation followed by image erosion. For dilation, a chosen structuring element, for instance a 3×3 pixel matrix, is marched over the input image. The image pixel corresponding to the center of the pixel matrix is replaced by the pixel of maximum intensity in the pixel matrix. Thus, when dilation is applied, bright objects appear to grow while the darker holes in the object tend to shrink. Erosion works in a manner opposite from dilation. When erosion is applied to a grey scale image, bright objects shrink in size, and dark holes within those objects become larger. The effect of grayscale morphological closing is to eliminate unwanted dark regions in the image smaller than the structuring element, while preserving bright regions. Conversely, the effect of morphological opening eliminates bright regions in the image smaller than the structuring element, while preserving dark regions. A person skilled in the art of digital image processing would know of many structuring element shapes and sizes, and many combinations of erosion and dilation to achieve the desired result. For example, a 3×3 pixel matrix can be used as a small element, while 15×15 pixel matrix can be used as a large element.

At step 415 the original image of the slide is compared with the background intensity image. The minimum of the original image and the background intensity image can be subtracted from the original image to eliminate variation in illumination across the slide.

At step 420 background subtracted images are shrunk down by a predefined scale factor. For example, a predefined scale factor of 50 may be used. The shrunken images can be stitched together in step 425. Thus, a single mosaic image representing the entire scan area can be created, and yet have a manageable file size.

At step 430 the mosaic image is converted into a binary image by automatic thresholding based on analysis of the grey level gradients around the modal grey level of the mosaic image. First, the modal grey level in the image (m) is calculated by analysis of the histogram of the image. Then, for each pixel in the image, the maximum gray level gradient (g) is calculated as the maximum gray level difference between the pixel and its neighbors:

$$g = \text{Max}[I_{i,j} - I_{k,l}] \quad \text{Eq. (1.1)}$$

where k=i−1, i, i+1; l=j−1, j, j+1.

The gradients from equation 1.1 are summed for all pixels in the image to calculate the sum Sg. Similarly, for each pixel in the image, the gradient is multiplied by the pixel's grey value, and summed for all pixels in the image to calculate sum Sgi. Then, the threshold can be estimated as:

$$T = m + S_{gi}/S_g \quad \text{Eq. (1.2)}$$

The threshold calculation can be made more robust by considering only the pixels with grey value above m and below m+(range/5), where range is the difference between the maximum and minimum grey levels in the image. Many other thresholding techniques, known to a person skilled in the arts, may also be used.

At step 435 a decision is made whether to perform coverslip detection. The preferred technique for identification of the coverslip is image analysis using Hough transforms to identify edges of the coverslip, details of which are described in relation to FIG. 5. The coverslip area may bound the area of interest for the colony detection, for the cases where the cell colonies are only present underneath the coverslip. For instance, once the location of a coverslip is detected, all the pixel values outside of the coverslip area can be set to zero, as shown at step 445. When the pixels in an area of image have a uniform zero value that area does not have to be searched for the colonies in the subsequent processing steps, thus the time required for colonies identification and a possibility of making colony identification mistakes can be reduced.

At step 450 the binary mosaic image is enhanced by morphological processing: closing followed by opening. Morphological image processing techniques can be useful for extracting image components that may better represent and describe region shapes. This operation joins interphase cells visible in the mosaic into clusters.

At step 455 colonies (e.g., clusters) in the binary image are identified via image analysis (e.g., region detection). Many detection methods may be used. For example, automatic size measurements may be performed on the identified objects. Wanted objects may be those having a size between a predetermined minimum and maximum number of pixels. Unwanted objects can be eliminated at step 460 based on their size and/or morphology, thus reducing the processing time and the possibility of making colony identification mistakes in the subsequent steps.

At step 465 the position, size, and binary image mask are recorded for the colonies that remained after the elimination done at step 460. The subsequent processing steps can ignore empty spaces between the recorded colonies of interest, thus further saving the processing time.

At step 470 a switch is made to a higher power objective (e.g. 10× or 20×) for the subsequent colony image acquisition.

At step 475 the recorded colonies positions from step 465 are used as the basis for a focus map, i.e. automatic focusing is only performed where there are identified colonies. Large empty spaces among the colonies can be ignored, thus minimizing the time required to produce a focus map.

At step 480 the slide is scanned again with a higher power objective using the focus map derived in step 475. If the coverslip detection as in step 440 has been performed, the scan area for subsequent analysis can be reduced to that defined by the coverslip. The scan area can also be reduced to the bounding box around the recorded colonies.

At step 485 for each high power image frame metaphase detection is performed. Metaphase is a phase of cell reproduction cycle in which condensed chromosomes, carrying genetic information, align in the middle of the cell before being separated into each of the two daughter cells. The chromosomes shorten and become visible under the microscope during this phase. The visibility of the shortened chromosomes may be further enhanced by staining the cells with dyes.

At step 490 each detected metaphase is assigned to a colony based on its proximity to the colony center of gravity, radius and/or binary mask.

Figure 5:
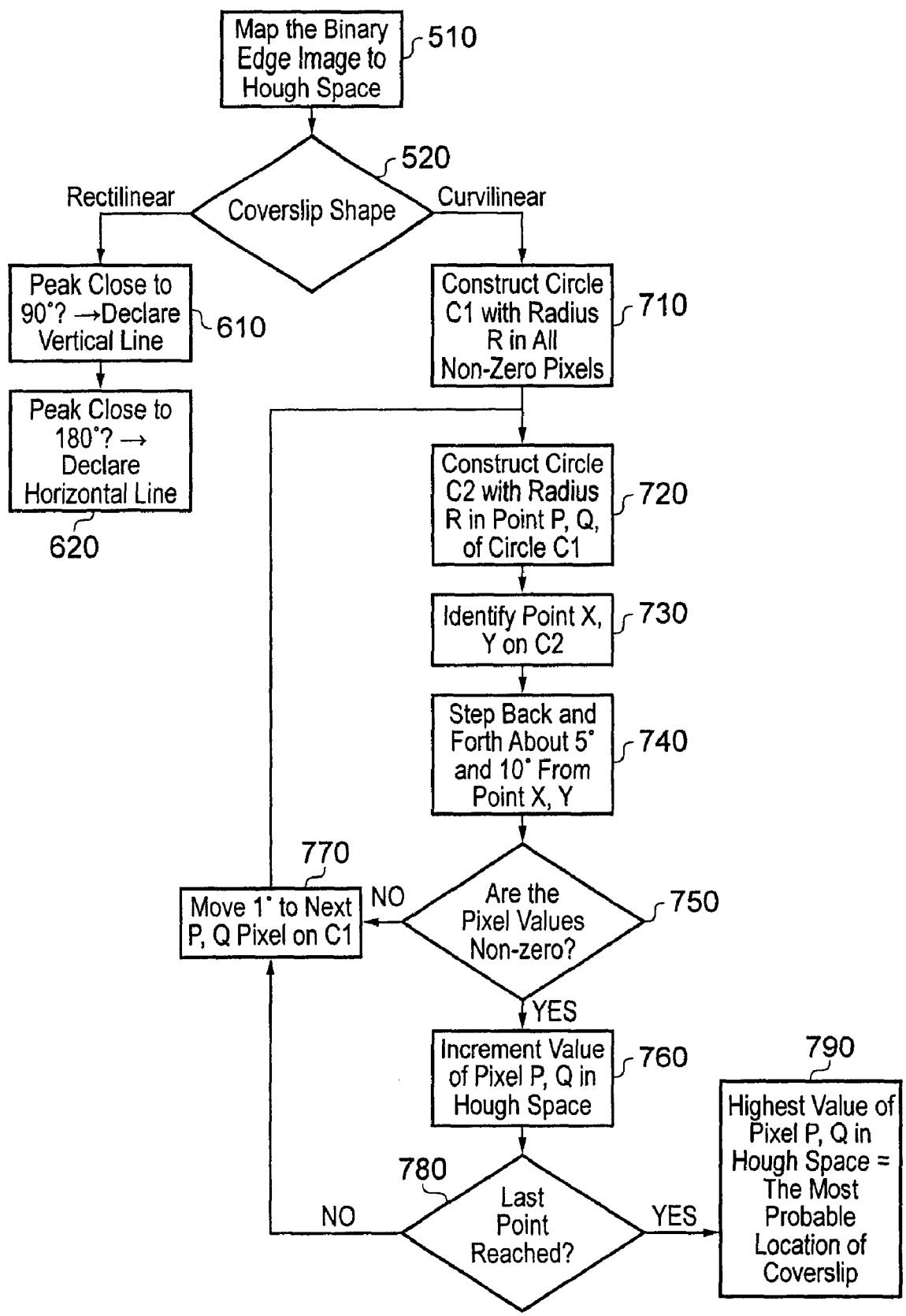
FIG. 5 shows a flowchart of a method for detection of the coverslip edge.

FIG. 5 shows a flowchart of coverslip detection according to one embodiment of the present invention. As explained above, coverslip detection may be beneficial in reducing the area of interest in the colony detections, thus reducing the slide processing time while also reducing false colonies detection. Furthermore, the area of slide image of interest can be enhanced by eliminating coverslip edges and the mounting compound from the subsequent image analysis.

At step 510 a binary edge image from step 430 of FIG. 4 is passed through a Hough transform to produce its counterpart in Hough space. A linear Hough transform for detecting straight lines, which can be used for detecting the edges of a rectilinear coverslip, is described below.

In the image space, the straight line can be written as:

$$y = mx + b \quad \text{Eq. (2.1)}$$

In Hough space, the characteristics of the straight line are not points x, y, but the slope parameter "m" and the intercept parameter "b." Thus, a straight line as in equation (2.1) can be represented as a point (b, m) in Hough space. However, vertical lines would give rise to unbounded values of the parameters "m" and "b." Therefore, for computational reasons it is better to parameterize the lines with two other parameters: "r" and "θ." The parameter "r" represents the distance between the line and the origin of a coordinate system, while "θ" is the angle of the vector from the origin to this closest point. Using this parameterization, the equation of a line can be written as:

$$r = x \cos\theta + y \sin\theta \quad \text{Eq. (2.2)}$$

It is therefore possible to associate each line of an image to a pair (r,θ). The (r,θ) plane can be referred to as Hough space for the set of straight lines in two dimensions.

An infinite number of lines can pass through a single point of the plane. If that point has coordinates $(x_o, y_o)$ in the image plane, then all the lines that go through it obey the following equation:

$$r(\theta) = x_o \cos\theta + y_o \sin\theta \qquad \text{Eq. (2.3)}$$

Equation (2.3) describes a sinusoidal curve in the $(r,\theta)$ plane. If the curves corresponding to two points are superimposed, the location (in the Hough space) where they cross corresponds to lines (in the original image space) that pass through both points. The Hough transform algorithm uses an array, sometimes called accumulator, to calculate the likelihood of the existence of a line $y=mx+b$ in the image space. For each pixel and its neighborhood, the Hough transform algorithm determines if there is enough evidence of an edge at that pixel. If so, it will calculate the parameters of that line, and then look for the accumulator's bin that the parameters fall into, and then increase the value of that bin. By finding the bins with the highest values, typically by looking for local maxima in the accumulator space, the most likely location of the lines in the image space can be found.

Although the version of the transform described above applies to finding straight lines, a similar transform can be used for finding any shape which can be represented by a set of parameters. A circle, for instance, can be transformed into a set of three parameters, representing its center and radius, so that the Hough space becomes three dimensional. For a circular coverslip with a known radius, Hough transform becomes a two parameter one, which can be executed following the steps as outlined above.

Returning back to FIG. 5, at step 520 a decision on specific processing steps for the image in Hough space is made depending on the shape of the coverslip: rectilinear or curvilinear. Although these coverslip shapes may be the most common, the method is not limited to them.

At steps 610 and 620 the processing of the rectilinear coverslip is described. The image in the Hough space is analyzed to identify peaks close to 90 and 180 degrees. These peaks represent lines close to horizontal and vertical in the binary edge image, respectively. The highest peaks represent the most likely locations of the horizontal and vertical edges of the coverslip. Various thresholds and knowledge of the dimensions of the coverslip can be used to help avoid or minimize false peak detections.

The processing of the curvilinear coverslip with known radius R is explained with reference to steps 710 to 790. At step 710 a circle C1 with radius R is constructed in all non-zero pixels of the image.

At step 720 point P, Q on circle C1 is selected and circle C2 having a center in point P, Q and having radius R is constructed.

At step 730 point X, Y on circle C2 is identified. Next, at step 740, values of the pixels on circle C2 in the vicinity of point X, Y are identified. The pixels that are located about 5° and 10° back and forth from point X, Y can be used, but other suitable angle values may be used.

At step 750 the values of the pixels identified in step 740 are evaluated. The non-zero values make the presence of circular coverslip centered in point P, Q more likely. Therefore, the counter associated with point P, Q in Hough space is correspondingly increased in step 760.

If the pixel values at step 750 were zero, then at step 770 a next point P, Q on circle C1 is chosen by moving along circle C1 for about 1° away from the previous point P, Q. Next, new circle C2 is constructed in new point P, Q (as in step 720) and the identification of the most likely position of the circular coverslip can continue as shown at steps 720-750.

At step 780 a check is performed to verify whether the last point on the last circle C1 is reached. If not, then step 770 is executed again by moving along circle C1 for about 1° away from the previous point P, Q, and proceeding back to step 720. If the last step on the last circle C1 was reached, the processing is finished. The point with the highest value of pixel P, Q in Hough space can be declared the most probable location of the center of the circular coverslip.

Figure 6A:
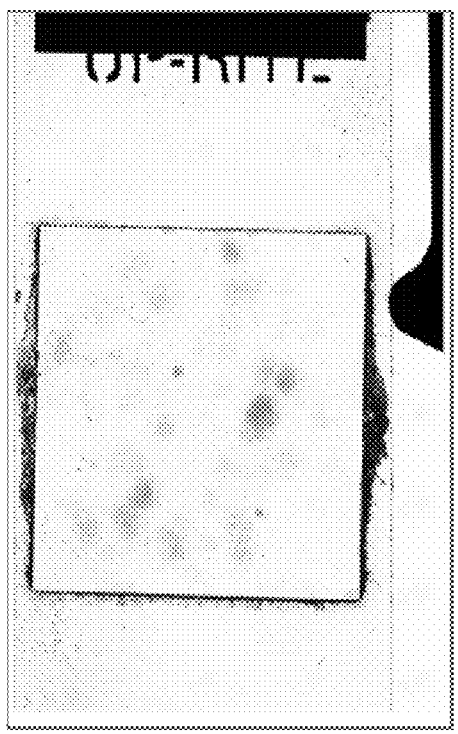
FIGS. 6A and 6B illustrate a Hough transform based coverslip edge detection for the rectangular and circular coverslips, respectively.
Figure 6A:
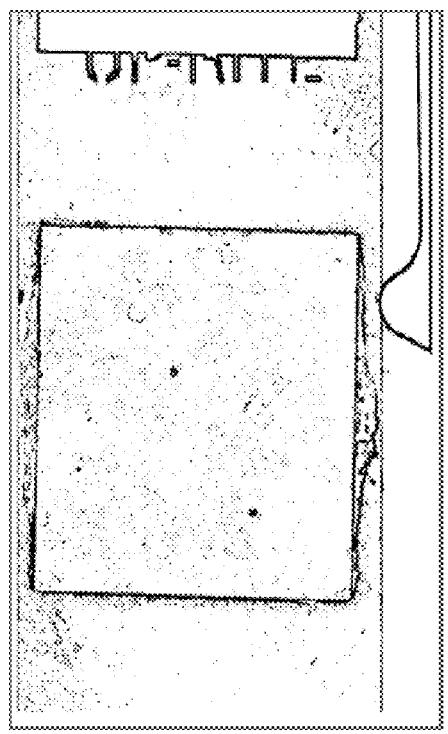
Figure 6A:
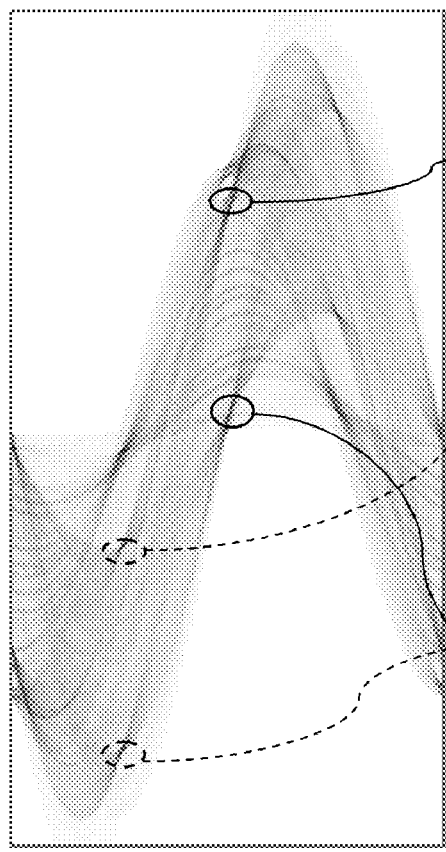
Figure 6A:
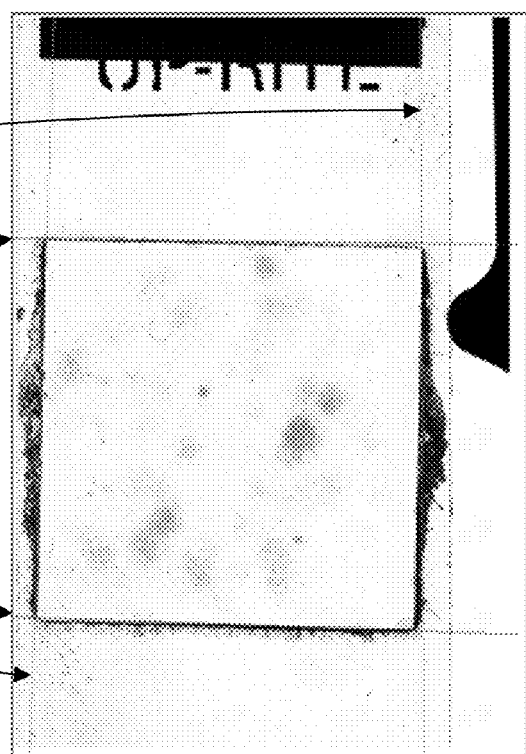
Figure 6B:
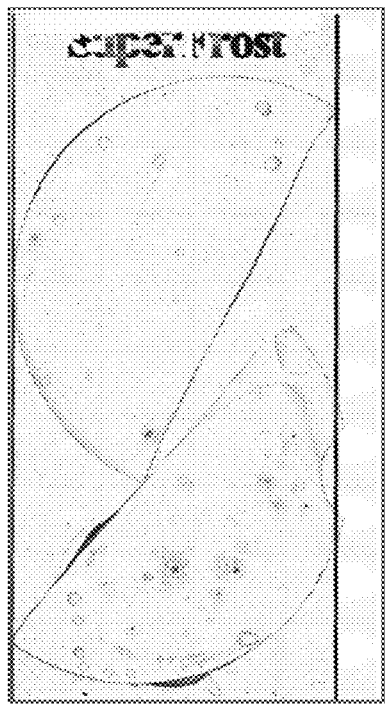
Figure 6B:
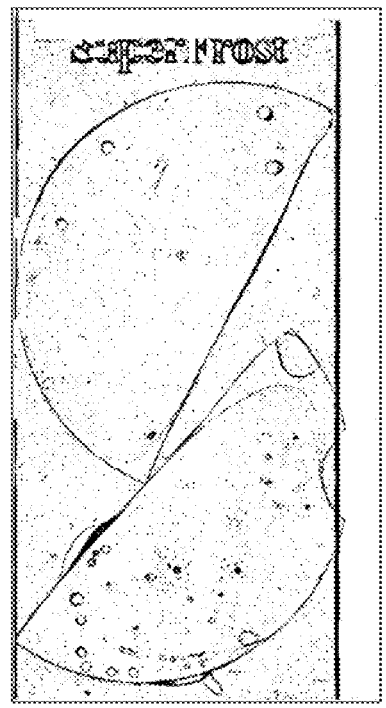
Figure 6B:
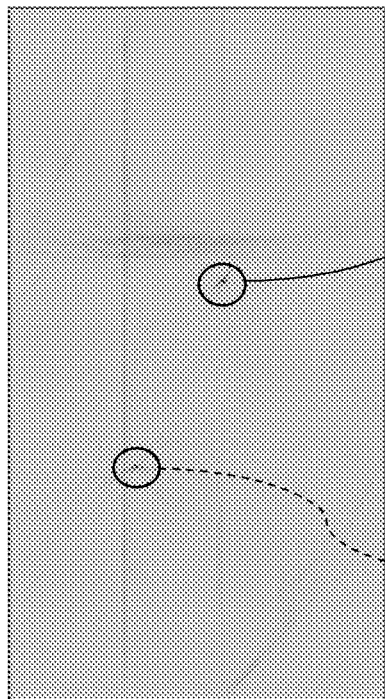
Figure 6B:
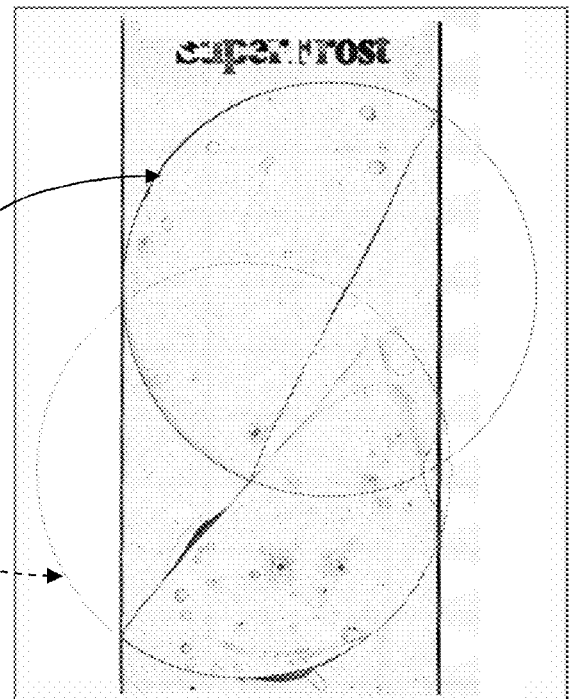

FIGS. 6A and 6B show examples of the method shown in FIG. 4 applied to the rectilinear and curvilinear coverslips, respectively. FIGS. 6A and 6B show four images each. The images in the upper left corners are the original digital image of the slides, as obtained in, for instance, step 425 of FIG. 4. To a human observer the edges of the coverslips may be obvious, but to a computer system they may not be obvious.

The images in the upper right corners are the binary images that were generated through a thresholding technique as in, for instance, step 430 of FIG. 4. These images can be transferred to the Hough space by a transformation as in, for instance, step 610 of FIG. 5. The resulting images in the Hough space are shown in the lower left corner of FIGS. 6A and 6B. The image in the Hough space can be analyzed as outlined in steps 610-620 (rectilinear coverslip) or steps 710-790 (circular coverslip).

The images in the lower right corners of FIGS. 6A and 6B show the identification of the coverslip edges. Using the reverse Hough transform, the peak coordinates in Hough space (the images in the lower left corners) can be converted back to the lines in the original image space, thus identifying the edges of the coverslips, which, in turn, may bound the regions of interest for the colonies detection. Furthermore, the images can be enhanced by eliminating coverslip edges and mounting compound from the image.

Figure 7:
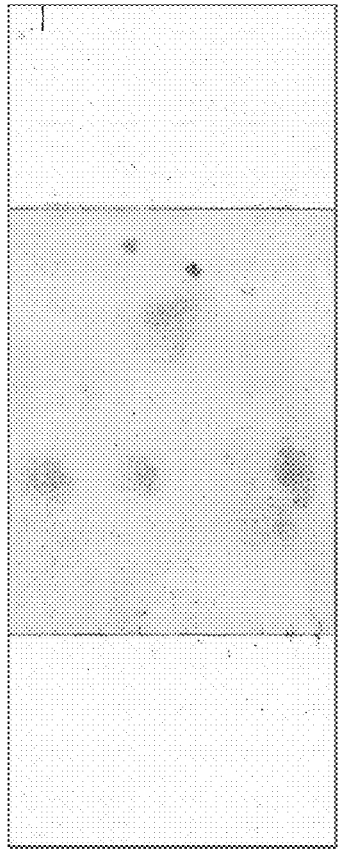
FIG. 7 illustrates colonies detection on a slide.
Figure 7:
Figure 7:
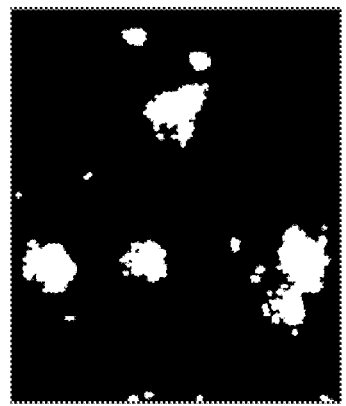

FIG. 7 illustrates an application of the method shown in FIG. 4. The leftmost image shows a slide with the rectangular coverslip. This image may be an input slide generated in step 425 of FIG. 4. The middle image in FIG. 7 shows the region of the slide that corresponds to the coverslip area. All pixel values outside of the coverslip area are set to zero, and thus excluded from the subsequent analysis. The middle image may be generated in step 445 of FIG. 4. The rightmost image in FIG. 7 shows detected colonies in a binary image, as in step 455 of FIG. 4. After the colonies are detected, the metaphase detection and assigning each metaphase to a colony can be performed, as in steps 485 and 490 of FIG. 4.

While the above invention is described in conjunction with a high throughput image capturing system, the embodiments of the present invention are also applicable to any slide analysis system to: identify where cells are located on the sample slide; identify the area where the system should perform focus mapping for accurate scanning; minimize high magnification scan time, and maximize system throughput by concentrating only on the areas where cells are present. Furthermore, while rectilinear and curvilinear coverslip edge detections are described in detail above, other coverslip shapes may also be detected using the embodiments of the present invention.

The above description is illustrative and is not restrictive, and as it will become apparent to those skilled in the art upon review of the disclosure, the present invention may be embodied in other specific forms without departing from the essential characteristics thereof. These other embodiments are intended to be included within the spirit and scope of the present invention. The scope of the invention should, therefore, be determined not with reference to the above description, but instead should be determined with reference to the following and pending claims along with their full scope of equivalents.

What is claimed is:

1. A method for an automatic detection of cell colonies, comprising:
    acquiring digital images of sub-areas of a slide;
    generating background intensity images;
    forming background-subtracted sub-area images by subtracting the minimum of a morphologically processed image and the original digital image from the original image;
    generating shrunk sub-area images by shrinking the background-subtracted sub-area images by a predefined scale factor;
    stitching the shrunk sub-area images into a composite image representing the entire slide;
    converting the composite image into a binary edge image by the application of an automatic thresholding technique;
    passing the binary edge image through a Hough transform to produce a Hough space transformed image;
    analyzing the Hough space transformed image to identify peaks representing a coverslip edge location;
    subjecting the Hough space transformed image to an inverse Hough transform to convert said peaks back to the edges of the coverslip in the binary edge image;
    setting to zero all pixels of the composite image outside of the coverslip area;
    morphologically processing the composite binary edge image;
    identifying colonies in the composite binary edge image;
    eliminating unwanted colonies from the composite binary edge image based on their size or morphology;
    recording the location, size, or binary image masks of the remaining colonies on the slide;
    generating a map of automatic focusing values over the remaining colonies on the slide using a high power objective;
    acquiring a plurality of high power images over the remaining colonies on the slide using a high power objective and the map of automatic focusing values;
    performing metaphase detection; and
    assigning each detected metaphase to a colony.

2. The method of claim 1 wherein said digital images are acquired by a digital camera with a low power or a high power objective at a fixed calibrated focus.

3. The method of claim 2 wherein said digital camera is a CCD camera.

4. The method of claim 2 wherein said low power objective is chosen from the range of 1.25 to 5.

5. The method of claim 2 wherein said high power objective is chosen from the range of 10 to 20.

6. The method of claim 1 wherein said morphological processing comprises:
    morphologically closing the sub-area image with a small structuring element; and
    morphologically opening the resulting image with a large structuring element.

7. The method of claim 1 wherein the composite image stitching is enhanced by closing with a small structuring element, followed by opening with a small structuring element and subtracting the result from the original composite image.

8. The method of claim 1 wherein said automatic thresholding technique is based on an analysis of the grey level gradients around a modal grey level of the composite image.

9. The method of claim 1 wherein said Hough transform is a linear Hough transform configured for a rectilinear coverslip, the Hough transform is based on polar coordinates of a line, said transformed image is analyzed to identify peaks close to 90° and 180° representing horizontal and vertical lines in the binary edge image, and said transformed image is subjected to an inverse Hough transform to convert said peaks close to 90° and 180° back to horizontal and vertical lines representing the edges of the coverslip in the binary edge image.

10. The method of claim 1 wherein said Hough transform is configured for a curvilinear coverslip, having a substantially circular shape with a known radius R, the Hough transform is based on a weighted circular Hough transform, said transformed image is analyzed to find the most probable locations of coverslip centers, and said transformed image is subjected to an inverse circular Hough transform to convert said most probable locations of coverslip centers back to the locations in the binary edge image.

11. The method of claim 10 wherein said transformed image is analyzed to find the most probable locations of coverslip centers by:
    (a) treating all non-zero pixels in the binary image as the centers of a circle C1 of radius R;
    (b) treating each point on circle C1 as the center P,Q of a circle C2 of radius R;
    (c) for each point X,Y on circle C2 stepping back about 5° and about 10° and stepping forward about 5° and about 10° starting from the point X,Y along the circle C2, and checking when the pixel at that location is non-zero in the binary image, and when it is, then incrementing the value of pixel at P,Q in the Hough space image;
    (d) moving to the next point on circle C1 in steps of about 1°, and repeating steps (b) and (c);
    treating the highest value of pixel at P,Q in the Hough image as the most probable location of the center of the circular shape coverslip.

12. The method of claim 1 wherein the composite image outside of the coverslip area is not used in generating a map of automatic focusing values.

13. The method of claim 1 wherein the composite image outside of the coverslip area is not used in colony detection.

14. The method of claim 1 wherein the composite image outside of the coverslip area is cropped to reduce the image to the area within the coverslip.

15. The method of claim 1 wherein assigning each detected metaphase to a colony is based on the metaphase proximity to the colony center of gravity, radius, and binary mask.

16. An apparatus for an automatic detection of cell colonies, comprising: an optical system comprising a digital camera for acquiring digital images of the slide, a computing unit for storing and processing the digital images of the slide, said computing unit executing a method so as to cause:
    images of sub-areas of a slide to be acquired by digital camera with a low power objective at a fixed calibrated focus;
    background intensity images to be generated;
    a background-subtracted sub-area images to be formed by subtracting the minimum of a morphologically processed image and the original digital image from the original image;
    shrunk sub-area images to be generated by shrinking the background-subtracted sub-area images by a predefined scale factor;
    the shrunk sub-area images to be stitched into a composite image representing the entire slide;

the composite image to be converted into a binary edge
image by the application of an automatic thresholding
technique;
the binary edge image to be passed through a Hough transform to produce a Hough space transformed image;
the Hough space transformed image to be analyzed to
identify peaks, representing coverslip edge location;
the Hough space transformed image to be subjected to the
inverse Hough transform to convert said peaks back to
the edges of the coverslip in the binary edge image;
all pixels of the composite image to be set to zero outside of
the coverslip area;
the composite binary edge image to be morphologically
processed;
colonies in the composite binary edge image to be identified;
unwanted colonies from the composite binary edge image
to be eliminated based on their size or morphology;
the location, size, or binary image masks of the remaining
colonies on the slide to be recorded;
a map of automatic focusing values over the remaining
colonies on the slide to be generated using a high power
objective;
a plurality of high power images to be acquired over the
remaining colonies on the slide using a high power
objective and the map of automatic focusing values;
metaphase detection to be performed; and
each detected metaphase to be assigned to a colony.

17. The apparatus of claim 16 wherein said digital camera is a CCD camera.

18. The apparatus of claim 16 wherein said low power objective is chosen from the range of 1.25 to 5.

19. The apparatus of claim 16 wherein the background subtraction is done by causing:
the sub-area image to be morphologically closed with a
small structuring element;
the resulting noise image to be morphologically opened
with a large structuring element;
the resulting noise image minimum of the sub-area and the
original digital image of that sub-area to be found.

20. The apparatus of claim 16 wherein the composite image stitches enhancement is done by closing with a small structuring element, followed by opening with a small structuring element and subtracting the result from the composite image.

21. The apparatus of claim 16 wherein said automatic thresholding technique is based on a predetermined grey level value.

22. The apparatus of claim 16 wherein said computing unit causes said Hough transform to be a linear Hough transform configured for a rectilinear coverslip, the linear Hough transform to be based on polar coordinates of a line, said transformed image to be analyzed to identify peaks close to 90° and 180° representing horizontal and vertical lines in the binary edge image, and said transformed image to be subjected to an inverse Hough transform to convert said peaks close to 90° and 180° back to horizontal and vertical lines representing the edges of the coverslip in the binary edge image.

23. The apparatus of claim 16 wherein said computing unit causes said Hough transform to be configured for a curvilinear coverslip having approximately circular shape with a known radius R, the transform to be based on a weighted circular Hough transform, said transformed image to be analyzed to find the most probable locations of coverslip centers, and said transformed image to be subjected to an inverse circular Hough transform to convert said most probable locations of coverslip centers back to the locations in the binary edge image.

24. The apparatus of claim 23 wherein said computing unit causes said transformed image to be analyzed to find the most probable locations of coverslip centers by:
(a) treating all non-zero pixels in the binary image as the center of a circle C1 of radius R;
(b) treating each point on circle C1 as the center P,Q of a circle C2 of radius R;
(c) for each point X,Y on circle C2 stepping back about 5° and about 10° and stepping forward about 5° and about 10° starting from the point X,Y along the circle C2, and checking if the pixel at that location is non-zero in the binary image, and if it is then incrementing the value of pixel at P,Q in the Hough image;
(d) moving to a next point on circle C1 in steps of about 1°, and repeating steps (b) and (c);
treating the highest value of pixel at P,Q in the Hough image as the most probable location of the coverslip.

25. The apparatus of claim 16 wherein the composite image outside of the coverslip area is not used in generating a map of automatic focusing values.

26. The apparatus of claim 16 the composite image outside of the coverslip area is not used in colony detection.

27. The apparatus of claim 16 wherein the composite image outside of the coverslip area is cropped to reduce the image to the area within the coverslip.

28. The apparatus of claim 16 wherein assigning each detected metaphase to a colony is based on the metaphase proximity to the colony center of gravity, radius, and binary mask.

29. A method for an automatic detection of slide coverslips, comprising:
acquiring digital images of sub-areas of the slide;
generating background intensity images;
forming background-subtracted sub-area images by subtracting the minimum of a morphologically processed image and the original digital image from the original image;
generating shrunk sub-area images by shrinking the background-subtracted sub-area images by a predefined scale factor;
stitching the shrunk sub-area images into a composite image representing the entire slide;
converting the composite image into a binary edge image by the application of an automatic thresholding technique;
passing the binary edge image through a Hough transform to produce a Hough space transformed image;
analyzing the Hough space transformed image to identify peaks representing a coverslip edge location;
subjecting the Hough space transformed image to an inverse Hough transform to convert said peaks back to the edges of the coverslip in the binary edge image; and
setting to zero all pixels of the composite image outside of the coverslip area.

30. The method of claim 29 wherein said digital images are acquired by a digital camera with a low power or a high power objective at a fixed calibrated focus.

31. The method of claim 30 wherein said digital camera is a CCD camera.

32. The method of claim 30 wherein said low power objective is chosen from the range of 1.25 to 5.

33. The method of claim 29 wherein the composite image stitching is enhanced by closing with a small structuring element, followed by opening with a small structuring element and subtracting the result from the composite image.

34. The method of claim 29 wherein said morphological processing comprises:
   morphologically closing the sub-area image with a small structuring element; and
   morphologically opening the resulting noise image with a large structuring element.

35. The method of claim 29 wherein said automatic thresholding technique is based on an analysis of the grey level gradients around a modal grey level of the composite image.

36. The method of claim 29 wherein said Hough transform is a linear Hough transform configured for a rectilinear coverslip, the linear Hough transform is based on polar coordinates of a line, said transformed image is analyzed to identify peaks close to 90° and 180° representing horizontal and vertical lines in the binary edge image, and said transformed image is subjected to an inverse Hough transform to convert said peaks close to 90° and 180° back to horizontal and vertical lines representing the edges of the coverslip in the binary edge image.

37. The method of claim 29 wherein said Hough transform is configured for a curvilinear coverslip, having a substantially circular shape with a known radius R, the Hough transform is based on a weighted circular Hough transform, said transformed image is analyzed to find the most probable locations of coverslip centers, and said transformed image is subjected to an inverse circular Hough transform to convert said most probable locations of coverslip centers back to the locations in the binary edge image.

38. The method of claim 37 wherein said transformed image is analyzed to find the most probable locations of coverslip centers by:
   (a) treating all non-zero pixels in the binary image as the centers of a circle C1 of radius R;
   (b) treating each point on circle C1 as the center P,Q of a circle C2 of radius R;
   (c) for each point X,Y on circle C2 stepping back about 5° and about 10° and stepping forward about 5° and about 10° starting from the point X,Y along the circle C2, and checking when the pixel at that location is non-zero in the binary image, and when it is, then incrementing the value of pixel at P,Q in the Hough space image;
   (d) moving to the next point on circle C1 in steps of about 1°, and repeating steps (b) and (c);
   treating the highest value of pixel at P,Q in the Hough image as the most probable location of the circular shape coverslip.

39. The method of claim 29 further comprising:
   morphologically processing the composite binary edge image;
   identifying colonies in the composite binary edge image;
   eliminating unwanted colonies from the composite binary edge image based on their size or morphology;
   recording the location, size, or binary image masks of the remaining colonies on the slide;
   generating a map of automatic focusing values over the remaining colonies on the slide using a high power objective;
   acquiring a plurality of high power images over the remaining colonies on the slide using a high power objective and the map of automatic focusing values;
   performing metaphase detection; and
   assigning each detected metaphase to a colony.

40. The method of claim 39 wherein said high power objective is chosen from the range of 10 to 20.

41. The method of claim 39 wherein the composite image outside of the coverslip area is not used in generating a map of automatic focusing values.

42. The method of claim 39 wherein the composite image outside of the coverslip area is not used in colony detection.

43. The method of claim 39 wherein the composite image outside of the coverslip area is cropped to reduce the image to the area within the coverslip.

44. The method of claim 39 wherein assigning each detected metaphase to a colony is based on the metaphase proximity to the colony center of gravity, radius, and binary mask.

45. An apparatus for an automatic detection of slide coverslips, comprising: an optical system comprising a digital camera for acquiring digital images of the slide, a computing unit for storing and processing the digital images of the slide, said computing unit executing a method so as to cause:
   images of sub-areas of a slide to be acquired by digital camera with a low power objective at a fixed calibrated focus;
   background intensity images to be generated;
   a background-subtracted sub-area images to be formed by subtracting the minimum of a morphologically processed image and the original digital image from the original image;
   shrunk sub-area images to be generated by shrinking the background-subtracted sub-area images by a predefined scale factor;
   the shrunk sub-area images to be stitched into a composite image representing the entire slide;
   the composite image to be converted into a binary edge image by the application of an automatic thresholding technique;
   the binary edge image to be passed through a Hough transform to produce a Hough space transformed image;
   the Hough space transformed image to be analyzed to identify peaks, representing coverslip edge location;
   the Hough space transformed image to be subjected to the inverse Hough transform to convert said peaks back to the edges of the coverslip in the binary edge image; and
   all pixels of the composite image to be set to zero outside of the coverslip area.

46. The apparatus of claim 45 wherein said digital camera is a CCD camera.

47. The apparatus of claim 45 wherein said low power objective is chosen from the range of 1.25 to 5.

48. The apparatus of claim 45 wherein the background subtraction is done by causing:
   the sub-area image to be morphologically closed with a small structuring element;
   the resulting noise image to be morphologically opened with a large structuring element;
   the resulting noise image minimum of the sub-area and the original digital image of that sub-area to be found.

49. The apparatus of claim 45 wherein the composite image stitches enhancement is done by closing with a small structuring element, followed by opening with a small structuring element and subtracting the result from the composite image.

50. The apparatus of claim 45 wherein said automatic thresholding technique is based on a predetermined grey level value.

51. The apparatus of claim 45 wherein said computing unit causes said Hough transform to be a linear Hough transform configured for a rectilinear coverslip, the linear Hough transform to be based on polar coordinates of a line, said transformed image to be analyzed to identify peaks close to 90° and 180° representing horizontal and vertical lines in the binary edge image, and said transformed image to be subjected to an inverse Hough transform to convert said peaks close to 90° and 180° back to horizontal and vertical lines representing the edges of the coverslip in the binary edge image.

52. The apparatus of claim 45 wherein said computing unit causes said Hough transform to be configured for a curvilinear coverslip having approximately circular shape with a known radius R, the linear Hough transform to be based on a weighted circular Hough transform, said transformed image to be analyzed to find the most probable locations of coverslip centers, and said transformed image to be subjected to an inverse circular Hough transform to convert said most probable locations of coverslip centers back to the locations in the binary edge image.

53. The apparatus of claim 52 wherein said computing unit causes said transformed image to be analyzed to find the most probable locations of coverslip centers by:
   (a) treating all non-zero pixels in the binary image as the center of a circle C1 of radius R;
   (b) treating each point on circle C1 as the center P,Q of a circle C2 of radius R;
   (c) for each point X,Y on circle C2 stepping back about 5° and about 10° and stepping forward about 5° and about 10° starting from the point X,Y along the circle C2, and checking if the pixel at that location is non-zero in the binary image, and if it is then incrementing the value of pixel at P,Q in the Hough image;
   (d) moving to a next point on circle C1 in steps of about 1°, and repeating steps (b) and (c);
treating the highest value of pixel at P,Q in the Hough image as the most probable location of the center of the coverslip.

54. The apparatus of claim 45 wherein said computing unit further causes:
   the composite binary edge image to be morphologically processed;
   colonies in the composite binary edge image to be identified;
   unwanted colonies from the composite binary edge image to be eliminated based on their size or morphology;
   the location, size, or binary image masks of the remaining colonies on the slide to be recorded;
   a map of automatic focusing values over the remaining colonies on the slide to be generated using a high power objective;
   a plurality of high power images to be acquired over the remaining colonies on the slide using a high power objective and the map of automatic focusing values;
   metaphase detection to be performed; and
   each detected metaphase to be assigned to a colony.

55. The apparatus of claim 54 wherein the composite image outside of the coverslip area is not used in generating a map of automatic focusing values.

56. The apparatus of claim 54 wherein the composite image outside of the coverslip is not used in colony detection.

57. The apparatus of claim 54 wherein the composite image outside of the coverslip area is cropped to reduce the image to the area within the coverslip 58. The apparatus of claim 54 wherein assigning each detected metaphase to a colony is based on the metaphase proximity to the colony center of gravity, radius, and binary mask.

* * * * *